US00PP22464P3

(12) United States Plant Patent
Clark et al.

(10) Patent No.: US PP22,464 P3
(45) Date of Patent: Jan. 24, 2012

(54) PEACH TREE NAMED 'WHITE DIAMOND'

(50) Latin Name: *Prunus persica*
Varietal Denomination: White Diamond

(75) Inventors: John Reuben Clark, Fayetteville, AR (US); James N. Moore, Fayetteville, AR (US)

(73) Assignee: The Board of Trustees of the University of Arkansas, Little Rock, AK (US)

( * ) Notice: Subject to any disclaimer, the term of this patent is extended or adjusted under 35 U.S.C. 154(b) by 0 days.

(21) Appl. No.: 12/802,655

(22) Filed: Jun. 11, 2010

(65) Prior Publication Data

US 2011/0307983 P1 Dec. 15, 2011

(51) Int. Cl.
*A01H 5/00* (2006.01)

(52) U.S. Cl. ..... Plt./196

(58) Field of Classification Search ..... Plt./196
See application file for complete search history.

(56) References Cited

U.S. PATENT DOCUMENTS

| | | | |
|---|---|---|---|
| PP86 | P | 2/1934 | Fruehwirth |
| PP15,159 | P3 | 9/2004 | Clark |
| PP17,742 | P3 | 5/2007 | Clark et al. |

OTHER PUBLICATIONS

Clark, J.R., et al., "'White Diamond' and 'White Cloud' Peaches," Hort. Science (2011) 46(4):665-667.

*Primary Examiner* — Susan McCormick Ewoldt
(74) *Attorney, Agent, or Firm* — Andrus, Sceales, Starke & Sawall, LLP

(57) ABSTRACT

Description and specification of a new and distinct peach tree cultivar named 'White Diamond' which originated from a hand-pollinated cross of Ark. 392 (female, non-patented, unreleased genotype)×'White River' (male, U.S. Plant Pat. No. 15,159) is provided. This new peach tree cultivar can be distinguished by its late-season maturity, firm flesh, low-acid flavor, large freestone fruits and resistance to bacterial spot disease.

3 Drawing Sheets

Latin name: *Prunus persica.*
Varietal denomination: 'White Diamond'.

BACKGROUND

A new cultivar of peach tree called 'White Diamond' is described herein. The new cultivar originated from a hand-pollinated cross of Ark. 392 (female, non-patented, unreleased genotype)×White River (male, U.S. Plant Pat. No. 15,159) made in 1994. The seeds resulting from this controlled hybridization were germinated and grown in a greenhouse between late fall 1994 and April 1995 and planted in a field near Clarksville, Ark. The seedlings fruited in the summer of 1998, and one seedling, designated Ark. 700, was selected for its late-season maturity, firm flesh, low-acid flavor, large freestone fruits and resistance to bacterial spot disease.

SUMMARY OF THE INVENTION

The new and distinct variety of peach originated from a hand-pollinated cross of Ark. 392 (female, non-patented, unreleased genotype)×White River (male, U.S. Plant Pat. No. 15,159) made in 1994 and located near Clarksville, Ark. (West-Central Arkansas).

The seeds resulting from this controlled hybridization were germinated in a greenhouse in the late fall 1994 and grown in a greenhouse in winter and early spring of 1995 and planted in a field in late April 1995 near Clarksville, Ark. The seedlings fruited during the summer of 1998 and one, designated Ark.

700, was selected for its late-season maturity, firm flesh, low-acid flavor, large, freestone fruits and resistance to bacterial spot disease.

During 1998, the original plant selection was propagated asexually, at the above-noted location, by budding onto standard peach rootstock variety>Lovell=(non-patented) and a test plot of two plants was established. Subsequently, larger test plantings have been established with asexually multiplied plants at two additional locations in Arkansas (Clarksville and Hope, Ark.) and at each location propagation was by budding from buds collected at the Clarksville, Ark. test plot. No incompatibility with 'Lovell' peach rootstock has occurred following budding. During all asexual multiplication, the characteristics of the original plant have been maintained and no aberrant phenotypes have appeared.

The new cultivar has been named the 'White Diamond' cultivar.

BRIEF DESCRIPTION OF THE PHOTOGRAPHS

The accompanying photographs show typical specimens of the new variety in color as nearly true as it is reasonably possible to make in a color illustration of this character.

DETAILED DESCRIPTION OF THE NEW CULTIVAR 'WHITE DIAMOND'

Figure 1:
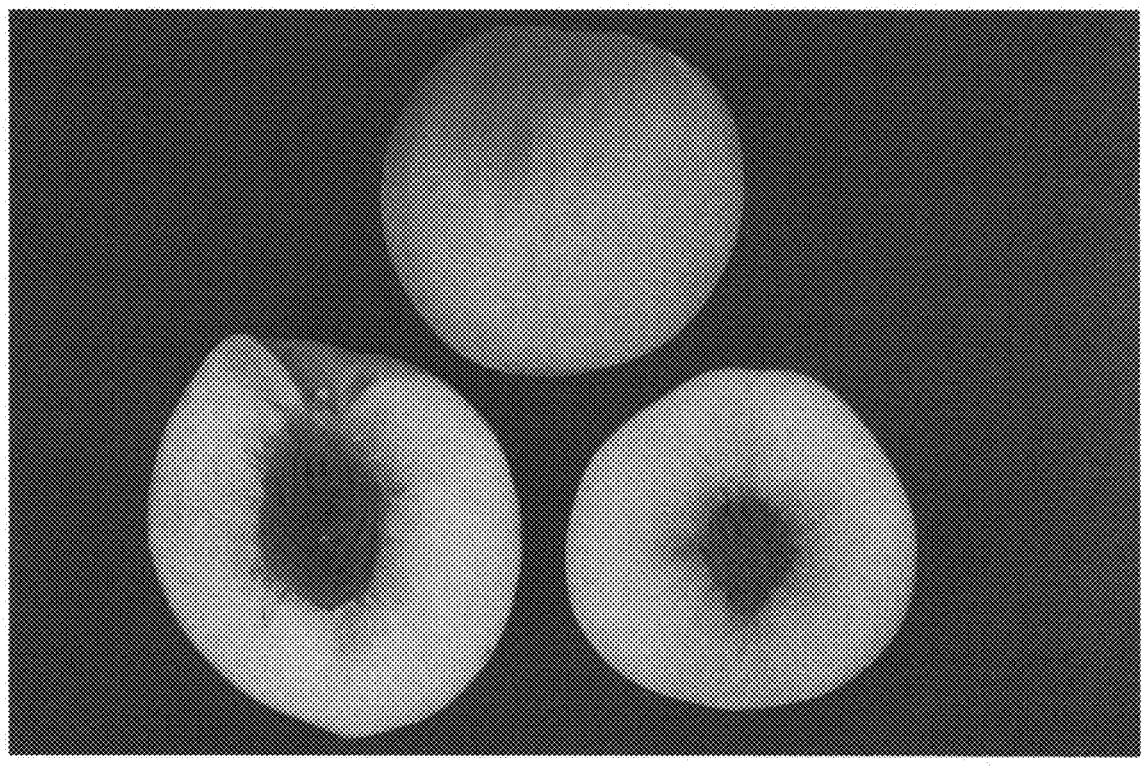
FIG. 1 is a photograph of a whole and longitudinally cut fruit of 'White Diamond' at maturity.
Figure 2:
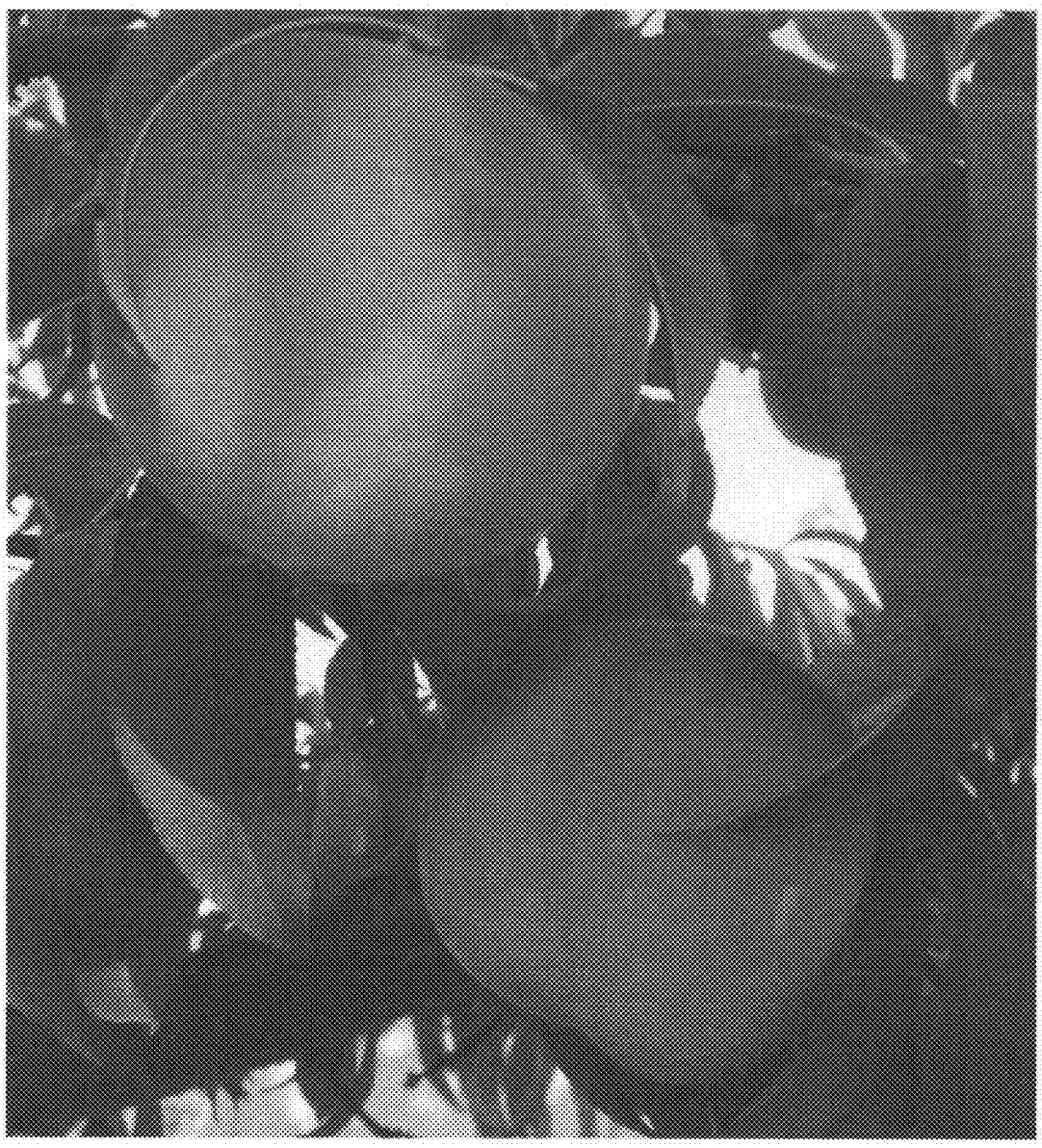
FIG. 2 is a photograph of mature fruit on a tree of 'White Diamond.'
Figure 3:
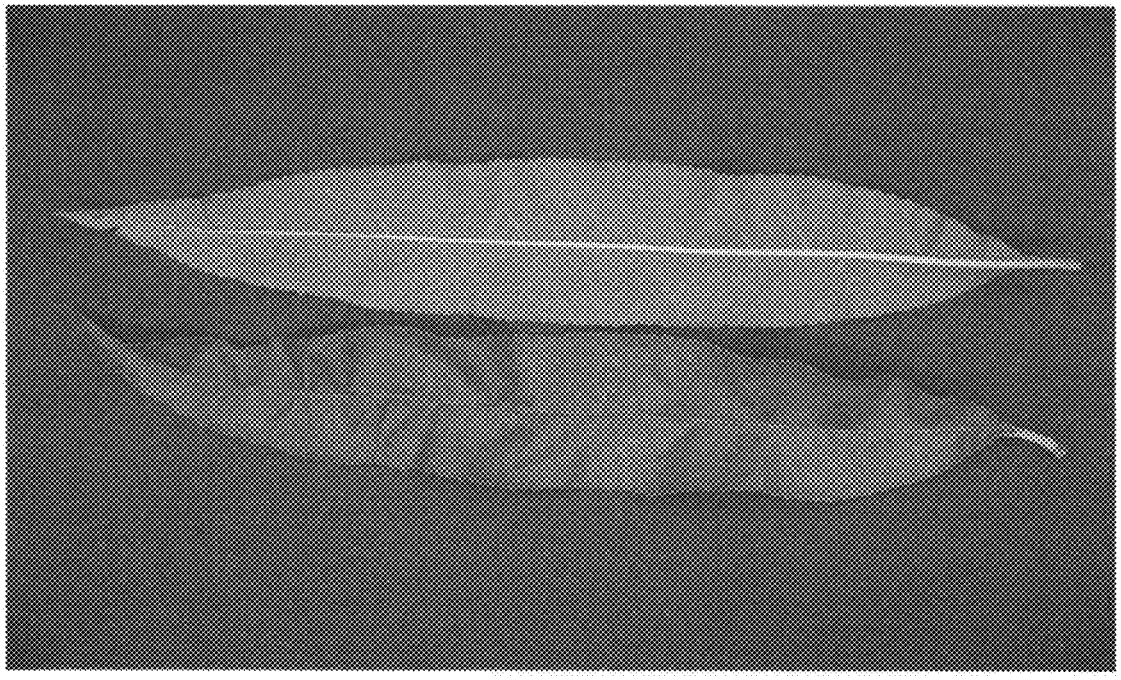
FIG. 3 is a photograph of the adaxial and abaxial sides of mature 'White Diamond' leaves.

Plants and fruit of this new cultivar differ phenotypically from its parents. The new cultivar is earlier ripening, has better flavor, more red skin color, is larger, and more resistant to bacterial spot disease than the parent Ark. 392. The new cultivar is different from parent 'White River' in that it is low-acid in flavor, ripens later, and has much firmer flesh. Both the parents and the new cultivar are the genus and species *Prunus persica*.

Plants of the new cultivar are vigorous and productive, and trees are standard in size, well-branched and symmetrical with a semi-spreading growth habit, comparable to other peach trees. Trees express a moderate to high level of resistance to both foliar and fruit infection of bacterial spot [*Xanthomonas campestris* pv. *pruni* (Smith) Dye] but in some years do not show complete immunity to this disease. Resistance of 'White Diamond' to bacterial spot disease is similar to the 'White County' (U.S. Plant Pat. No. 17,742). The new cuitivar consistently exhibits more resistance to bacterial spot than the white peach cultivars 'Carolina Belle' (not patented) and 'Nectar' (U.S. Plant Pat. No. 86).

'White Diamond' has 10% bloom on average March 17, 3 days before that of 'White County' and 'White River'. Full bloom date is also 3 days earlier than the comparison cultivars. Flowers are showy for the new cultivar. No winter cold injury has been observed on wood or buds of the new variety in Arkansas tests were minimum temperatures have reached 7° F. (−14° C.) during evaluation. Chilling requirement to break dormancy is estimated to be 800 hours below 45° F. (7° C.).

Fruit of the 'White Diamond' cultivar ripens late-season, averaging 29 July, 14 days later than 'White County,' and 10 days later than 'White River'. Fruits of the new cultivar have not been observed to have split pits, a serious fruit disorder of some peach cultivars. Fruit yields of the new cultivar have been good and have averaged higher or comparable to 'White River' and higher than 'Nectar'.

The fruit of the 'White Diamond' cultivar is round, without a prominent tip but occasionally has a slight suture bulge. Fruits are attractive with an average 87% bright red blush, and 13% white skin with a white or cream skin background color. Fruit finish is good with no blemishes. The fruit skin has average to light pubescence like other peaches. The flesh of the fruit is white in color and has slight red pigment in the flesh, mostly around the stone or pit. Flesh is melting but very firm until fully mature when it softens. The fruit is a freestone, in that the flesh does not adhere to the pit at maturity.

Fruit size is medium-large averaging 200-230 g. 'White Diamond' fruits are slightly smaller than 'White River', which average 260 g. The fresh fruit rates excellent in flavor, and was rated highly in evaluations and comparable in flavor to 'White County' and 'White River'. The flavor of 'White Diamond' is sweet and low-acid, with a distinct white peach aroma. Fruits average 14.5% soluble solids, higher than 'White County' (13.1%) and 'White River' (12.5%).

The following is a detailed description of the botanical and pomological characteristics of the subject peach. Color data are presented in Royal Horticultural Society Colour Chart designations. Where dimensions, sizes, colors, and other characteristics are given, it is to be understood that such characteristics are approximations of averages set forth as accurately as practicable.

Plants used for botanical data were eight years old and grown on a fine sandy loam soil with trickle irrigation near Clarksville, Ark. Trees were trained to an open-center training system and dormant pruned annually. The exception to this is that yield data was collected on trees six years old and trained to a perpendicular V training system. Fruits on all trees were thinned to approximately 6-8 inches between fruits 4-5 weeks after full bloom. The trees were fertilized near budbreak (late March on average) with complete or nitrogen fertilizer. Weeds were controlled with pre- and postemergence herbicides. Routine commercial fungicide and insecticide applications were applied to the trees, but no bactericides (for control of bacterial diseases such as bacterial spot disease) were applied. The descriptions reported herein are from specimens grown near Clarksville, Ark.

Plant:

*Size.*—Mature trees (5 years of age and older) average 3.4 to 3.6 m in height and 4.8 to 6.0 m in spread or width, and a semi-upright growth habit, as grown on 'Lovell' rootstock using an open center training system commonly used on peaches. Tree size is comparable to that of the 'White County' and 'White River' cultivars.

*Growth.*—Vigorous, symmetrical form, good canopy development. Vigor is comparable to that of the 'White County' and 'White River' cultivars.

*Productivity.*—Productive and consistent from year to year. Yield measured in kg/tree on six-year old, perpendicular V-trained trees was 9.9 kg for 'White Diamond', 9.3 kg/tree for 'White River', and 3.9 kg/tree for 'Nectar'.

*Cold hardiness.*—Wood and dormant buds hardy to at least −13° C. (7° F.) as this is the coldest the trees have been exposed to at the test site. Hardiness may exceed this temperature.

*Disease resistance.*—Leaves and fruit are resistant but not immune to bacterial spot under growing conditions where bacterial spot infection is often very severe on susceptible genotypes. No bactericides were used in the development or evaluation of the instant cultivar. Evidence of bacterial spot infection was less than that of 'Carolina Belle' and 'Nectar' in all years of evaluation. A commercial fungicide program was utilized in orchards used in the development and evaluation of the instant variety, thus no resistance to brown rot or scab, the other common diseases at Clarksville, Ark., was determined.

*Insect resistance.*—Insecticides were applied to orchards used in the development of the new cultivar to control the common insects at the location including oriental fruit moth, plum curculio, stinkbug, tarnished plant bug, lesser peach tree borer, and greater peach tree borer. Therefore no insect resistance was determined in its testing.

Foliage/shoots/branches:

*Shoots.*—Smooth; dormant-season shoot (branch): length 36.2 cm; diameter at base 0.5 cm; diameter at midpoint 0.4 cm; diameter at terminal 0.3 cm. Dormant-season shoot color: Greyed-Red Group (178A).

*Leaves.*—Simple, alternate, glabrous, lanceolate, petiolate, deciduous. Venation pinnate; base acute; terminal or apex acuminate; margin serrated. Mature leaf size: length 18.5 cm; width midpoint 4.0 cm. Leaf serrations — 4/cm. Mature leaf color: abaxial — Yellow-Green Group (147B); adaxial — Green Group (137A); and anthocyanin not present on abaxial or adaxial side of mature leaves on midrib or other location. Young leaf color: abaxial — Green Group (137D); adaxial — Green Group (137D); anthocyanin not present on abaxial or adaxial side of young leaves on midrib or other location. Petiole length — mature leaf: 1.3 cm. Leaf glands: reniform, 4 per leaf usually, located at base of leaf blade and top of petiole. Leaf glands are 0.09 cm in width and 0.18 cm in length.

*Buds.*—Number of leaf buds per 15 cm: 7, evenly distributed along the shoot. Number of flower buds per 0-15 cm from terminal: 10. Mature shoot internode length: base 1.28 cm; midpoint 2.6 cm; terminal 1.0 cm.

Bark (of mature trunk of tree):

*Color.*—Greyed-Green Group (197C).

*Texture.*—Rough.

Trunk:

*Diameter.*—16.6 cm (at 25 cm above ground level).

Flowers: Bloom occurs prior to vegetative bud break; solitary to occasional double individual flowers at a single node; perfect; self-fertile.

*Date of bloom.*—First, 16 March; full, 23 March; 3 days before 'White County' and 'White River' for each bloom characteristic.

*Size.*—Diameter fully open 3.5 cm.

*Type.*—Showy.

*Color (petals).*—Adaxial: Red-Purple Group (65B) to Red-Purple (65A); abaxial: Red-Purple Group (65B) to Red-Purple Group (65A).

*Petal dimensions.*—Length: 1.9 cm; width 1.7 cm.

*Petal texture.*—smooth.

*Petals per flower.*—5.

*Pedicel length.*—0.5 cm.

*Length of pistil.*—1.7 cm.

*Stamens.*—Average 53/flower with pollen present, fertile, and abundant.

*Ovary.*—pubescent.

Fruit:

*Size.*—Medium-large, avg. 200-230 g; diameter stem end 6.4 cm, equator 7.6 cm, blossom end 5.6 cm; length base to apex 7.1 cm.

*Shape.*—Rounded, symmetrical; fruits are without pronounced tip but slight suture bulge.

*Skin.*—Lightly pubescent (fuzzy); attractive; ground color Yellow Group (11C) with blush color Red Group (46A) over 87% of surface on average.

*Flesh.*—Color Yellow-White Group (158C); freestone; smooth, melting texture but very firm until fully ripe when texture becomes melting; good firmness, and can be harvested with good flavor and sweetness prior to flesh softening. Firmness when measured by a fruit pressure tester (using a McCormick model FT327 fruit pressure tester, 11 mm diameter probe, McCormick Fruit Tree Co., Yakima, Wash.) on unpeeled fruit had average firmness value of 6.6 kg. Excellent eating quality; flavor sweet, low-acid, with pronounced white peach flavor and aroma.

*Pedicel length.*—0.6 cm.

*Pedicel diameter.*—0.3 cm.

*Pedicel color.*—Yellow-Green Group (145A).

*First harvest date.*—29 July; ripening of individual fruit is uniform; harvest period approximately 12 days.

*Tendency of pit to split.*—No split pits observed.

*Soluble solids.*—14.5%.

*Fruit juice pH.*—5.9.

*Titratable acidity.*—0.80 g/L expressed as malic acid.

Pit/stone:

*Size.*—Length 3.9 cm; diameter (midpoint) 2.5 cm.

*Shape.*—Almond.

*Color.*—Greyed-Orange Group (165A) with stone red-colored areas Red Group (46A).

Kernel:

*Size.*—Length 1.9 cm; diameter varies with dryness of the kernel but is up to 1.2 cm.

*Shape.*—Oval.

*Color.*—Greyed-Orange Group (164B).

Uses: Fresh consumption; not evaluated for drying or other uses.

The cultivar: The most distinctive features of the new variety are late-season maturity, firm flesh, low-acid flavor, large, freestone fruits and resistance to bacterial spot disease.

We claim:

1. A new and distinct cultivar of peach tree named 'White Diamond,' substantially as illustrated and described.

* * * * *